US008658085B2

(12) United States Patent
Kristiansson et al.

(10) Patent No.: US 8,658,085 B2
(45) Date of Patent: Feb. 25, 2014

(54) METHOD FOR IRRADIATING OBJECTS

(75) Inventors: Anders Kristiansson, Lund (SE); Lars Ake Näslund, Furulund (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 539 days.

(21) Appl. No.: 12/000,297

(22) Filed: Dec. 11, 2007

(65) Prior Publication Data

US 2008/0138243 A1    Jun. 12, 2008

Related U.S. Application Data

(60) Provisional application No. 60/874,284, filed on Dec. 12, 2006.

(30) Foreign Application Priority Data

Dec. 11, 2006  (SE) ...................................... 0602650

(51) Int. Cl.
*A61L 2/00*  (2006.01)
(52) U.S. Cl.
USPC ......... 422/22; 422/121; 422/186; 250/455.11
(58) Field of Classification Search
USPC ............ 422/22, 23, 32, 121, 186; 250/432 R, 250/455.11, 492.3; 34/611
See application file for complete search history.

(56) References Cited

U.S. PATENT DOCUMENTS

| 4,439,686 A | 3/1984 | Cheever |
| 2004/0089820 A1 * | 5/2004 | Rangwalla et al. ........ 250/492.3 |

FOREIGN PATENT DOCUMENTS

| CN | 101297376 A | 10/2009 |
| EP | 1 232 760 A1 | 8/2002 |
| EP | 1 356 828 A1 | 10/2003 |
| EP | 1 481 693 A2 | 12/2004 |
| EP | 1 518 563 A1 | 3/2005 |
| EP | 1956608 A1 | 8/2008 |
| JP | 2002-171949 | 6/2002 |
| JP | 2002-171949 A | 6/2002 |
| JP | 2005-247427 A | 9/2005 |
| JP | 2006-314407 A | 11/2006 |
| JP | 2007-113936 A | 5/2007 |
| JP | 2008-082919 A | 4/2008 |
| RU | 2 091 080 C1 | 9/1997 |
| WO | WO 96/40297 A1 | 12/1996 |

(Continued)

OTHER PUBLICATIONS

International-Type Search Report for ITS/SE06/00593 dated Jun. 20, 2007.

(Continued)

*Primary Examiner* — Walter D Griffin
*Assistant Examiner* — Timothy Cleveland
(74) *Attorney, Agent, or Firm* — Buchanan Ingersoll & Rooney PC

(57) ABSTRACT

The invention relates to a method for irradiating partly formed packages (10) with electron beam irradiation from at least one electron beam sterilizing device (18), characterized in that it comprises: providing at least one partly formed package (10) to be irradiated in a gaseous environment, and exposing the gaseous environment to a pre-determined pressure regulation cycle and exposing the partly formed package (10) to irradiation at least during a portion of said pressure regulation cycle. The invention also relates to a device for realizing said method. The invention further relates irradiation of a packaging material web.

14 Claims, 5 Drawing Sheets

(56) References Cited

FOREIGN PATENT DOCUMENTS

| WO | WO 98/42385 A1 | 10/1998 |
| WO | WO 00/55884 A1 | 9/2000 |
| WO | WO 02/075771 A1 | 9/2002 |
| WO | WO 2004110868 A1 * | 12/2004 |

OTHER PUBLICATIONS

English language translation of Russian Official Action dated Nov. 17, 2011 issued in the corresponding Russian Patent Application No. 2009126559.

Notice of Reasons for Rejection dated Dec. 6, 2011 issued in the corresponding Japanese Patent Application No. 2009-540200.

Supplementary European Search Report and European Search Opinion issued by European Patent Office on Dec. 16, 2012 in corresponding European Application No. 07835196.

Communication Pursuant to Article 94(3) EPC issued by the European Patent Office on Jul. 20, 2012 in corresponding European Application No. 07835196.

First Office Action issued by the State Intellectual Property Office of P.R.C. on Feb. 29, 2012 in corresponding Chinese Application No. 200780045869.6.

* cited by examiner

METHOD FOR IRRADIATING OBJECTS

The present invention refers to a method and a device for irradiating objects such as partly formed packages and packaging material webs with electron beam irradiation.

TECHNICAL BACKGROUND

Within the food packaging industry it has for a long time been used packages formed from a web or a blank of packaging material comprising different layers of paper or board, liquid barriers of for example polymers and gas barriers of for example thin films of aluminium. Another type of packages that are used in the food packaging industry is packages made from polymer material and manufactured through for example blow-moulding.

To extend the shelf-life of the products being packed it is prior known to sterilize the web before the forming and filling operations, and to sterilize the partly formed packages (ready-to-fill packages, RTF packages) before the filling operation. Depending on how long shelf-life is desired and whether the distribution and storage is made in chilled or ambient temperature, different levels of sterilization can be chosen. Usually, the level "commercially sterile" is applied for packages aimed for ambient temperature.

One way of sterilizing a web is chemical sterilization using for example a bath of hydrogen peroxide. Similarly, a ready-to-fill package can be sterilized by hydrogen peroxide, preferably in gas phase.

Another way of sterilizing packaging material is to irradiate it by means of electrons emitted from an electron beam emitting device, such as for example an electron beam generator. Such sterilization of a web of packaging material is disclosed in for example the international patent publications WO 2004/110868 and WO 2004/110869. Similar irradiation of ready-to-fill packages is disclosed in the international patent publication WO 2005/002973. The above applications are hereby incorporated by reference.

An exemplary system for sterilizing packages by electron beam technology includes an electron beam sterilizing device for emitting an electron beam along a path. The device is connected to an electron beam generator that is connected to a high voltage power supply and a filament power supply. The latter transforms power from the high voltage power supply to a suitable input voltage for a filament of the generator. The filament can be housed in a vacuum chamber. In operation, electrons e⁻ from the filament are emitted along an electron beam path in a direction towards a target. A grid around the filament is used for diffusing the electron beam into a more uniform beam, and for focusing the electron beam towards the target. Beam absorbers and magnetic fields can also be used to shape the electron beam. The electrons are exiting the sterilizing device through an electron exit window.

A system like this may as well also be used for other purposes than sterilization, for instance for curing of inks and coatings.

However, a disadvantage using irradiation is that much of the energy supplied to the system is lost when the electrons hit molecules in the surrounding environment (such as the air) and the energy is absorbed. Because of that it is difficult to make the electrons travel long distances, and therefore it is also sometimes difficult to provide a uniform electron beam dose to the object to be irradiated. It may for example sometimes be difficult to reach the portions of the object located most distant the electron beam generator.

Further, to obtain a sufficient irradiation level, the irradiation time has to be relatively long. This is inefficient from two perspectives. Firstly, the production time is affected, and in high speed production a long irradiation time is of course a disadvantage. Secondly, the longer irradiation time the more energy is used, and this considerably affects the cost.

SUMMARY OF THE INVENTION

Therefore, an object of the invention has been to provide a method for irradiating objects with electron beam irradiation with which the irradiation will be made in shorter time and with which the dose will be uniform.

The object is achieved with a method comprising the steps of providing at least one partly formed package to be irradiated in a gaseous environment, and exposing the gaseous environment to a pre-determined pressure regulation cycle and exposing the partly formed package to irradiation at least during a portion of said pressure regulation cycle.

By regulating the pressure in the gaseous environment it is possible to increase or decrease the number of molecules in the gas, and thereby regulate the distances and the main direction that the electrons travel. This is made in a cycle that can be optimized for the type of object to be irradiated and the irradiation cycle used.

If the pressure is reduced there will be a reduced number of molecules in the surrounding gaseous environment which will give the electrons a possibility of travelling more straight and for a longer distance, i.e. the electrons will reach longer. This will make it easier to reach portions or spots located far away from the electron beam generator. The effectiveness of the radiation increases and the irradiation can be made in less time. If the gas is air the reduced number of molecules will have a further advantage in that the amount of ozone created is reduced.

The pressure regulation cycle can be designed in many different ways depending on the type of object to be irradiated. The cycle may for instance involve multiple pressure changes, i.e. a predetermined sequence of pressure reductions and/or increases.

In a presently preferred embodiment of the invention the pressure regulation cycle involves at least changing from a first pressure to a second pressure. The first pressure is the initial pressure in the gaseous environment, and the second pressure is either higher or lower than the first pressure. Preferably, the second pressure is being lower than the first pressure. In this way the above advantages are obtained.

In a further preferred embodiment the method comprises the step of delimiting the environment around the partly formed package to be irradiated by providing an irradiation chamber. In this way the volume of gas to be regulated is limited and controllable.

In yet a further preferred embodiment the method comprises exposing the gas in the irradiation chamber to said pre-determined pressure regulation cycle.

In another preferred embodiment the method comprises the step of temporarily closing the irradiation chamber. In this way the different pre-defined pressures are more easily obtained.

In a preferred embodiment the method further comprises the steps of filling the partly formed package with content after irradiation, and thereafter sealing the partly formed package so that it thereby forms a sealed package.

The object is also achieved with a method for irradiating a web of packaging material. The method is characterized in that it comprises the steps of continuously conveying the web through a gaseous environment having a first pressure, the electron beam sterilizing device being provided in connection with said environment, and keeping a pre-determined second pressure at least in the environment nearest the sterilizing device during irradiation of the web. In this way the pressure near the sterilizing device may be kept at a pre-defined and suitable pressure for obtaining an effective irradiation.

In a preferred embodiment the second pressure is being lower than the first pressure.

The object is also achieved by a method for irradiating a web of packaging material, said method being characterized in that it comprises the steps of conveying the web through a gaseous environment, the electron beam sterilizing device being provided in connection with said environment, exposing at least the environment nearest the sterilizing device to a pre-determined pressure regulation cycle, and during irradiation exposing at least a portion of the web to said pressure regulation cycle.

In a preferred embodiment the pressure regulation cycle involves at least changing from a first pressure to a second pressure.

In a further preferred embodiment the second pressure is being lower than the first pressure.

In another preferred embodiment said portion of the web being provided with an opening arrangement.

In a preferred embodiment the method comprises the step of delimiting the environment around the portion of the web to be irradiated by providing an irradiation chamber.

In a preferred embodiment the method comprises the step of providing an irradiation chamber in the form of a narrow tunnel through which the web is passed and into which the irradiation from the sterilizing device is directed.

In a preferred embodiment the method comprises the step of providing means for achieving the second pressure at least in the environment nearest the sterilizing device, the means being provided upstream and downstream of the sterilizing device.

In a preferred embodiment the means are at least an upstream inlet nozzle and a downstream inlet nozzle provided in the tunnel, which nozzles are adapted to inject air flows into the tunnel to create an ejector effect.

In a preferred embodiment the method further comprises the steps of forming the irradiated web into a tube by overlappingly sealing the longitudinal edges of the web, filling the tube with content, and transversally sealing the tube to form cushions.

The object of the invention is further achieved with a device for irradiating partly formed packages. Said device comprising an irradiation chamber enclosing a gaseous environment, said irradiation chamber being adapted to receive at least one partly formed package to be irradiated, the electron beam sterilizing device being provided in connection with said environment, and means for exposing the gaseous environment to a pre-determined pressure regulation cycle at least during irradiation of the package.

In a preferred embodiment said means for exposing the gaseous environment to a pre-determined pressure regulation cycle are adapted to create a pressure regulation cycle at least involving changing from a first pressure to a second pressure, the second pressure being lower than the first pressure.

In a further preferred embodiment it comprises means for temporarily closing the irradiation chamber.

The object of the invention is further achieved by a device for irradiating a web of packaging material. Said device comprises an irradiation chamber enclosing a gaseous environment having a first pressure, means for continuously conveying the web through said gaseous environment, the electron beam sterilizing device being provided in connection with said environment, and means for keeping a pre-determined second pressure at least in the environment nearest the sterilizing device during irradiation of the web.

In a preferred embodiment the second pressure is being lower than the first pressure.

The object of the invention is further achieved by a device for irradiating a web of packaging material. Said device comprises an irradiation chamber enclosing a gaseous environment of a first pressure, means for conveying the web through said gaseous environment, the electron beam sterilizing device being provided in connection with said environment, and means for exposing the gaseous environment to a pre-determined pressure regulation cycle at least during irradiation of a portion of the web.

In a preferred embodiment said means for exposing the gaseous environment to a pre-determined pressure regulation cycle are adapted to create a pressure regulation cycle at least involving changing from a first pressure to a second pressure, the second pressure being lower than the first pressure.

BRIEF DESCRIPTION OF THE DRAWINGS

In the following, presently preferred embodiments of the invention will be described in greater detail, with reference to the enclosed drawings, wherein like reference numerals have been used to designate like elements, in which.

The same reference numerals are used for similar elements in the different embodiments.

DESCRIPTION OF PREFERRED EMBODIMENTS

Figure 1:
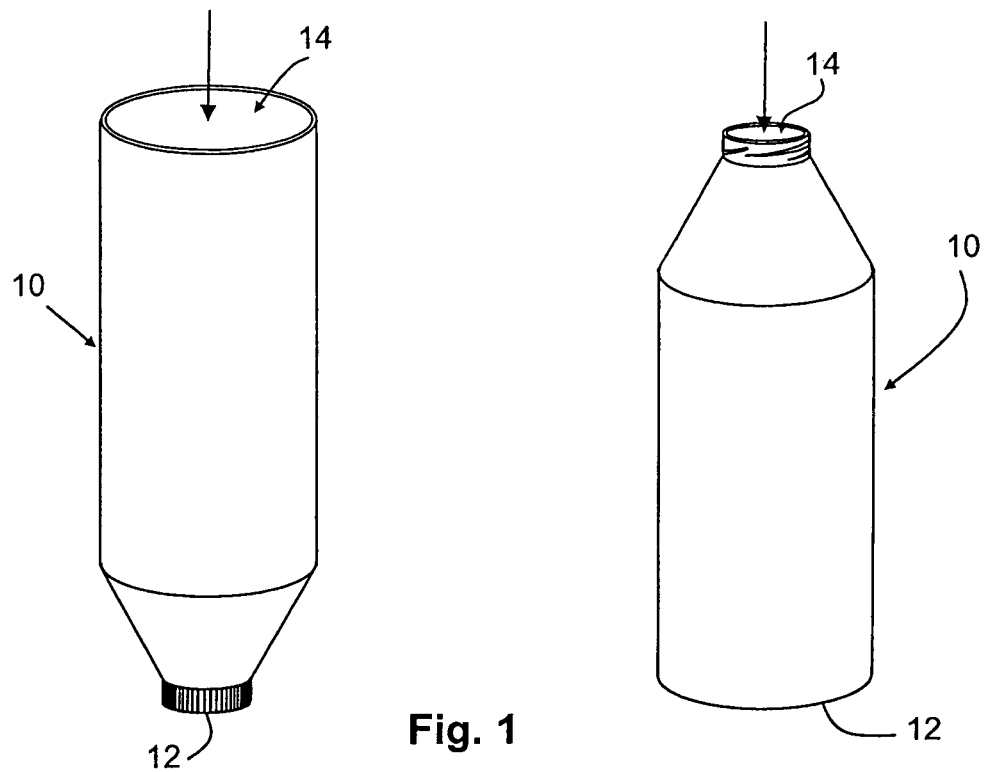
FIG. 1 schematically shows views of two ready-to-fill packages.

First an embodiment of the invention will be described which relates to irradiation of objects in the form of ready-to-fill packages in a packaging machine. In this embodiment the irradiation is made for sterilization purposes. FIG. 1 shows two examples of partly formed packages, denoted with the reference number 10, to be irradiated by the method of the invention. Generally, partly formed packages are normally closed in one end 12 and have an opening 14 in the other end. The closed end 12 can be formed as a bottom or top and the opening 14 can be an open end of a package sleeve, which will later be sealed, or for example a pour opening surrounded by a neck of a closure, which later will be provided with a cap or the like. The package example to the right in the figure has a sealed bottom end and an opening in the top in the form of a pour opening surrounded by threaded neck of a closure. This package may be a package manufactured through blow-moulding of a polymer material, for example PET. Said package will be sterilized through its pour opening. The package example to the left has an open (bottom) end and is provided in the other end with a top and a sealed closure. This package may be a package made from a polymer top and a sleeve of packaging material comprising different layers of paper or board, liquid barriers of for example polymers and gas barriers of for example thin films of aluminium. Said package will be sterilized through its open bottom end, i.e. the open end of the package sleeve.

Figure 2:
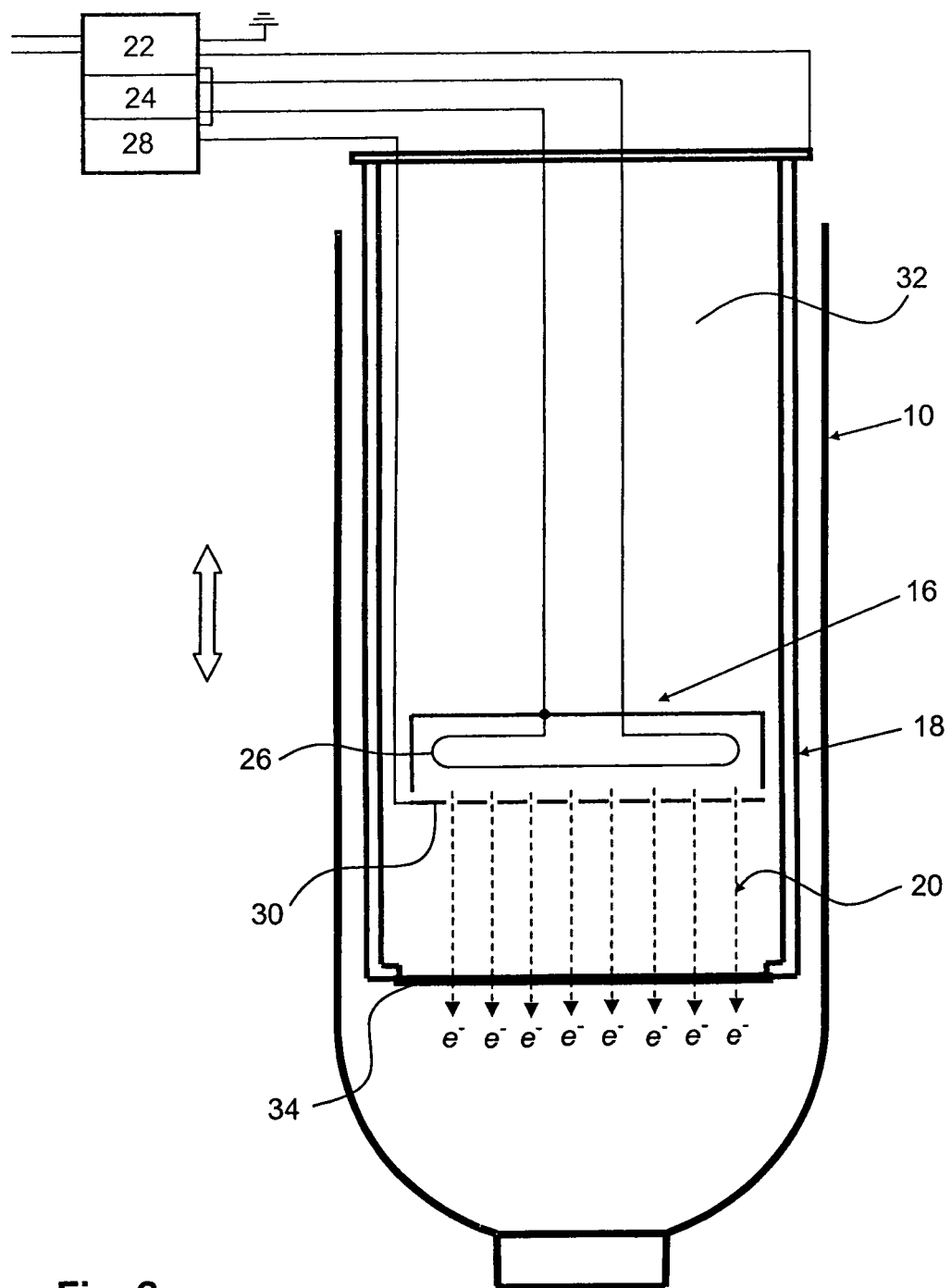
FIG. 2 schematically shows an exemplary system for irradiating a target in the form of a ready-to-fill package with an electron beam, FIG. 3 schematically shows a first embodiment of a device according to the invention, FIG. 4 schematically shows a second embodiment of a device according to the invention, FIG. 5 schematically shows a third embodiment of a device according to the invention, and FIG. 6 schematically shows a fourth embodiment of a device according to the invention.

In the following, and with reference to FIG. 2, an exemplary electron beam generator 16, an exemplary electron beam sterilizing device 18 for sterilizing ready-to-fill packages 10 and the concept of electron beam sterilization will be briefly described. The electron beam generator 16 comprises means for emitting an electron beam 20 along a path and it is connected to the sterilizing device 18 which distributes the beam 20 to the package 10.

Normally, an electron beam generator 16 is connected to a high voltage power supply 22, suitable for providing sufficient voltage to drive the electron beam generator 16 for the desired application. The electron beam generator 16 is also connected to a filament power supply 24, which transforms power from the high voltage power supply 22 to a suitable input voltage for a filament 26 of the generator 16. In addition, the high voltage power supply 22 includes a grid control 28 for controlling a grid 30 of the electron beam generator 16.

Electron beam generators used in the sterilization of packages are generally denoted low voltage electron beam units, which units normally have a voltage below 300 kV. In the disclosed design the accelerating voltage is in the order of 70-90 kV. This voltage results in kinetic (motive) energy of 70-90 keV in respect of each electron.

The filament 26 can be made of tungsten and can be housed in a vacuum chamber 32. In an exemplary embodiment, the vacuum chamber 32 can be hermetically sealed. In operation, an electrical current is fed through the filament 26 and the electrical resistance of the filament causes the filament 26 to be heated to a temperature in the order of 2000° C. This heating causes the filament 26 to emit a cloud of electrons $e^-$. The electrons are emitted along an electron beam path in a direction towards the target area, i.e. in this case the inside of the package 10. The grid 30, placed between the filament 26 and an electron beam exit window 34, is provided with a number of openings and is used for diffusing the electron beam 20 into a more uniform beam, and for focusing the electron beam 20 towards the target area.

In the embodiment shown the electron beam generator 16 means is housed in the electron beam sterilizing device 18, in the vacuum chamber 32 thereof. The sterilizing device 18 is, as mentioned, further provided with an electron exit window 34. The window 34 can be made of a metallic foil, such as for example titanium, and can have a thickness in the order of 4-12 μm. A supporting net (not shown) formed of aluminium or copper supports the foil from inside of the electron beam generator 16. The electrons are exiting the vacuum chamber 32 through the exit window 34.

In this embodiment the sterilizing device 18 with the electron beam generator 16 inside has the form of a cylinder with a substantially circular cross section and the exit window 34 is being located in a first end of the cylinder. The sterilizing device 18 may be designed in many other ways with regard to number and shape of the electron exit window(s) and the outer shape of the device.

A support (not shown) is provided for supporting the object. The support can for example be a conventional carrier of a conveyor which transports the package 10 through a sterilization unit in a packaging machine. During sterilization of a package 10 like the one to the left of FIG. 1, the package 10 may be placed upside down (i.e. the top is located downwards) in the support.

Generally, during sterilization a relative movement is performed between the package 10 and the sterilizing device 18. Either the sterilizing device 18 is lowered into or around the package 10, or the package 10 is raised to surround the device 18, or each is moving towards each other. To accomplish such the support may be either stationary or adapted to perform a motion towards and from the sterilizing device 18.

In the second end of the sterilizing device 18 incorporating the electron beam generator 16 there are means (not shown) provided for fastening it to a preferred element in the surroundings. For example such means can be means for suspending the sterilizing device 18 or the electron beam generator 16 from the inner top wall of a sterilization unit or irradiation chamber with the electron beam exit window 34 facing downwards in a direction towards the package 10.

In addition, the second end is provided with means (not shown) for providing a relative motion (see arrow) between the package 10 and the sterilizing device 18 for bringing them to a position or in a motion in which said device 18 is located at least partly in or around the package 10 for treating it.

The relative movement can be made in many conventional ways, and it will not be further described.

An example of the method according to the invention comprises the steps of providing at least one partly formed package to be irradiated in a gaseous environment, and exposing the gaseous environment to a pre-determined pressure regulation cycle and exposing the partly formed package to irradiation at least during a portion of said pressure regulation cycle. A device for carrying out the method is generally described as a device comprising an irradiation chamber enclosing a gaseous environment. Said irradiation chamber is adapted to receive at least one partly formed package to be irradiated. The described electron beam sterilizing device is being provided in connection with said environment, and there are means for exposing the gaseous environment to a pre-determined pressure regulation cycle at least during irradiation of the package. The method and the device will now be described in more detail.

The gaseous environment preferably comprises air, most preferably sterile air, but may constitute another gas such as for example an inert gas, for instance helium or nitrogen. Another alternative, which is suitable if the pressure regulation cycle corresponds to a temporary pressure decrease, is that the environment is air, but that an inert gas is supplied in small doses, i.e. a low flow, when the pressure is lowered. This will be further described later in relation to FIG. 6.

Figure 3:
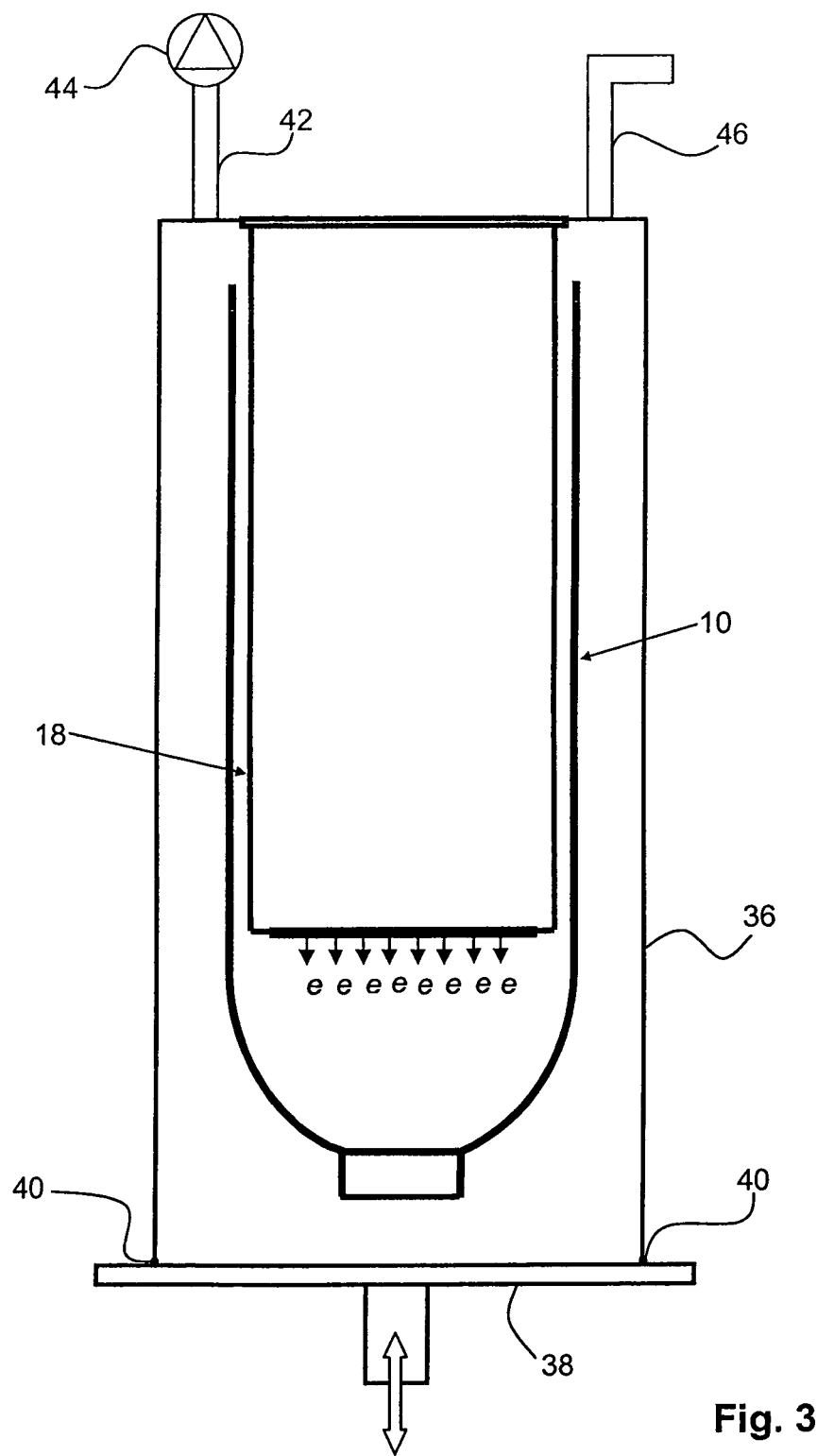

FIG. 3 shows an exemplary irradiation chamber 36. In a receiving state the irradiation chamber 36 is open in its bottom for receiving a package 10. Further, there are means provided for temporarily closing the irradiation chamber 36. In this example there is provided a lid 38 which is temporarily closed after a package 10 has been received in the chamber 36. In the intersection area between the chamber walls and the lid 38 there is preferably arranged vacuum seals 40 or other types of sealing.

From the inner top wall of the irradiation chamber 36 the electron beam sterilizing device 18 is suspended. Upon loading of the package 10 in the irradiation chamber 36 the package 10 will be raised to surround the electron beam sterilizing device 18. After loading of the package 10 the open chamber bottom will be closed by the lid 38, as can be seen in FIG. 3.

To enable a pressure regulation, in this case a temporary pressure decrease, in the irradiation chamber 36 the chamber is connected to means 44 for reducing the pressure. Such means 44 may be a pump that is able to suck out the air, such as a vacuum pump. The pump is connected to the chamber through a duct 42. In addition, the chamber 36 is provided with a duct 46 connected to a sterile air source (not shown). Sterile air is supplied when the irradiation is substantially finished before opening the lid 38. This is to make sure that no uncontrolled (and potentially contaminated) air is sucked into the chamber 36 from outside when the lid 38 is opened.

During the pressure regulation cycle the vacuum pump 44 will create the pre-determined reduction of the pressure in the chamber 36, and during at least during a portion of said pressure regulation cycle the package 10 will be exposed to irradiation by the electron beam sterilizing device 18.

After the sterilization has been performed the lid 38 is opened and the package 10 is lowered and conveyed out of the chamber 36, and a new package is supplied to the irradiation chamber 36. Thus, the relative movement that was earlier described is at least partly made when loading and unloading packages.

After the sterilization the partly formed packages 10 are filled with content, and thereafter they are sealed to form a sealed package. The portions of the machine performing these steps are not shown in FIG. 3.

In an alternative embodiment the "lid" is instead the package conveyor or package support, and the irradiation chamber has the form of a moveable cover or hood in which the sterilizing device is attached. During sterilization the hood is lowered to surround the package, and the electron beam sterilizing device is at the same time lowered into the package.

Figure 4:
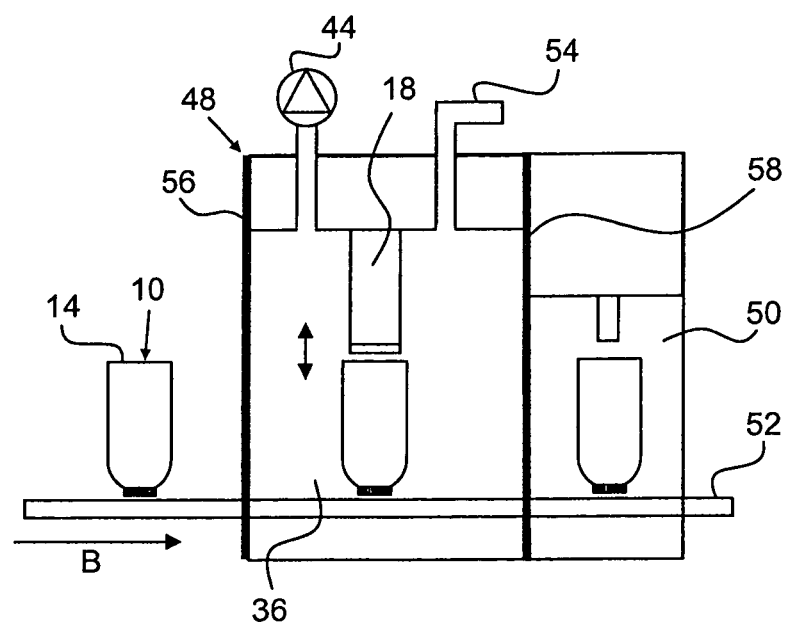

FIG. 4 shows a second embodiment of a device for irradiation of partly formed packages 10 in a packaging machine. The figure shows a schematic sterilization unit 48 comprising an irradiation chamber 36 and a filling chamber 50. The sterilization unit 48 comprises a conveyor 52 which is adapted to transport packages 10 through the unit 48. The arrow B illustrates the conveying direction. First the packages 10 are transported through the irradiation chamber 36 to be sterilized and then through the filling chamber 50 to be filled with a product. Said filling chamber 50 can be part of any suitable type of package filling system. For example a linear filling system or a rotary filling system can be used. The filling system will not be described in more detail. After filling the packages 10 are conveyed further to a sealing station where the packages are sealed in their still open end 14.

Further, there is provided means 44 for enabling a pressure regulation. In this case the pressure regulation constitutes a temporary pressure decrease and the means is a pump 44, for example a vacuum pump, in connection with the irradiation chamber 36. To sustain the reduced pressure, the irradiation chamber 36 is provided with two locks 56, 58. The locks are represented by thick black lines in the figure. One lock 56 is situated between the surrounding environment outside the sterilizing unit 48 and one lock 58 is situated between the irradiation chamber 36 and the filling chamber 50. The locks 56, 58 are of any conventional type and are airtight in a closed state. Further, the irradiation chamber 36 comprises a sterile air intake.

A package 10, arranged with its top directed downwards, is entering the irradiation chamber 36 through the first lock 56 to the left in FIG. 4 and is transported to the sterilizing device 18. Both locks 56, 58 are closed and the pressure within the chamber 36 is decreased and said sterilizing device 18 is lowered a suitable distance into the package 10, from the shown raised position, and irradiates the inside of the package. The package 10 is exposed to the irradiation for a predetermined time, which time is dependent on the relative movement between the package 10 and the sterilizing device 18. In the end of the sterilization the sterilizing device 18 is raised again and the package 10 is ready to proceed to the next chamber 50. Before the lock 58 to the filling chamber 50 is opened sterile air may be supplied to the irradiation chamber by a duct 54. However, the filling chamber 50 is commercially sterile. When the lock 58 is opened the package 10 is conveyed into the filling chamber 50 and filled, whereafter the package 10 is conveyed to a sealing station to be sealed. In this case the package 10 is sealed in that the open end 14 of the package sleeve is squeezed and transversally sealed by heat in a conventional way.

Figure 5:
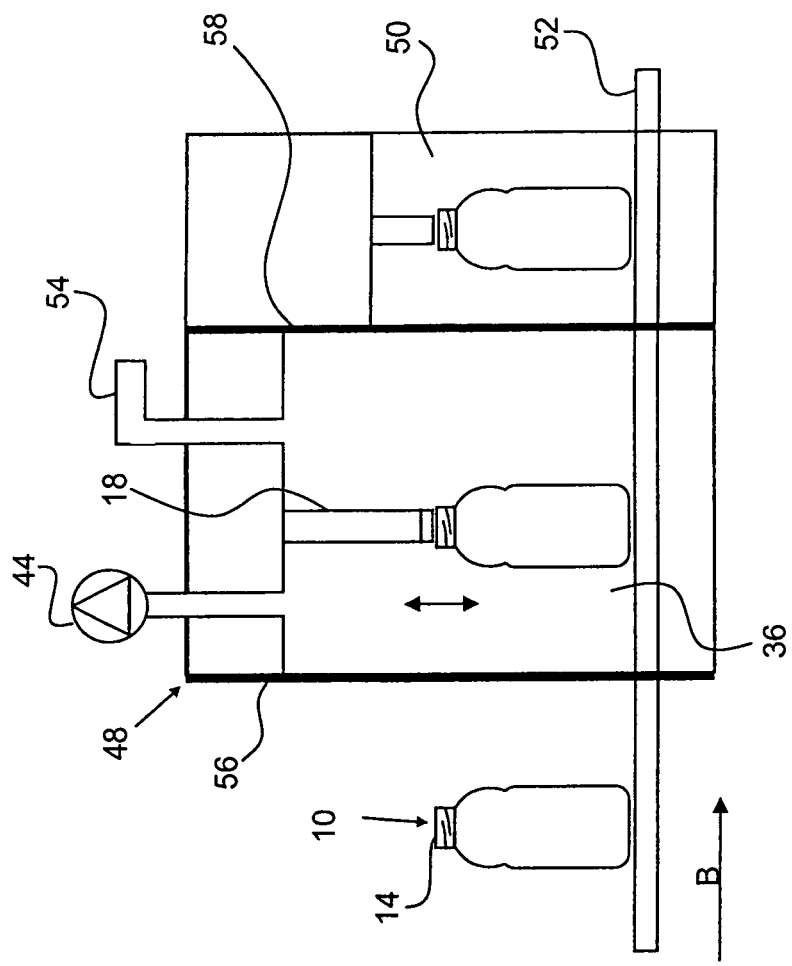

A third embodiment is shown in FIG. 5. Said embodiment is similar to the second embodiment, but the package to be sterilised is in this case a blow-moulded polymer package 10 in the form of a bottle. The package is arranged with its top directed upwards. The irradiation is made through the open pour opening of the package, and the package and/or the sterilizing device 18 is moved in relation to each other. After sterilization, when the lock 58 is opened, the package 10 is conveyed into the filling chamber 50 and filled. Afterwards, the package 10 is conveyed to a sealing station to be sealed. In this case the package 10 is sealed in that the still open pour opening 14 is provided with a cap.

According to the invention the gaseous environment is exposed to a pre-determined pressure regulation cycle and the object is exposed to irradiation at least during a portion of said pressure regulation cycle. The pressure regulation as such will now be described.

The pressure regulation cycle comprises a pressure regulation made during a pre-determined time interval that suits the irradiation cycle. During this cycle the pressure should be changing at least from a first pressure to a second pressure. The first pressure is the initial pressure in the gaseous environment, and the second pressure is either higher or lower than the first pressure.

The pressure regulation within the pressure regulation cycle may be arbitrarily chosen, but will have an effect on the efficiency of the irradiation. Generally, at least one pressure decrease is chosen to accomplish a considerable efficiency increase. Tests have shown that halving the pressure will give rise to an efficiency increase of the electron beam sterilizing device which makes it possible to substantially halving the time needed for irradiating an object. However, it is of course also dependent on the design of the object and the chosen irradiation degree, which can for example be "commercially sterile", which is common within the packaging industry. Further, tests made with an electron beam sterilizing device used for sterilizing packaging material have shown that only about 5% of the energy supplied to the electron beam sterilizing device actually reaches the surface layer of the packaging material. About 30% of the energy is caught in the material of the exit window and its support and the rest is caught by the air or reaches the inner layers of the packaging material. If halving the pressure about 10-12% of the energy supplied to the electron sterilizing device reaches the surface layer of the packaging material. This considerably affects the time needed for sterilization.

In an embodiment the pressure regulation cycle involves regulating the pressure so that the second pressure will be within a range of $1/10$ of the first pressure to $9/10$ of the first pressure. In another embodiment the pressure is regulated so that the second pressure will be within a range of $1/4$ of the first pressure to $3/4$ of the first pressure. In a further embodiment the pressure is regulated so that the second pressure will be within a range of $1/3$ of the first pressure to $2/3$ of the first pressure. In yet another embodiment the pressure is regulated so that the second pressure will be approximately $1/2$ of the first pressure.

In a preferred embodiment this pressure regulation cycle involves a temporary pressure decrease. Such can be accomplished in many different ways. One way is to decrease the pressure before starting the irradiation, and then the lower pressure is kept until the irradiation is substantially finished.

An alternative is to start decreasing the pressure at substantially the same time as starting irradiating the object. Once the lower pressure is reached it may be either kept throughout the remaining irradiation time, or it may be slowly raised again until the irradiation is finished or the original pressure is reached. A further alternative is to decrease the pressure before starting the irradiation, and then slowly raise the pressure again until the irradiation is finished or the original pressure is reached. It is easily understood that the number of different possible regulation cycles is very large. For example, any decreases and increases may be made instantly, continuously or stepwise. There may as well be provided for several pressure changes during the regulation cycle. In an ideal case the pressure is changed in relation to the form of the object to be irradiated and in relation to the relative movement made between the electron beam irradiation device and the object. For example, if a package like the one to the right in FIG. 1 is to be irradiated, the electron beam irradiation device will be lowered into the package through the pour opening. A possibly omptimised pressure regulation cycle may comprise starting the irradiation and the lowering of the irradiation device at a first pressure corresponding to a first pressure e.g. atmospheric pressure. This is to obtain a sufficient spreading of the electrons at the shoulder, or top, section of the package. When the irradiation device is further lowered into the package the pressure may be decreased to a second pressure so that the electrons travel more straight and reach to the bottom of the package. Upon raising the irradiation device, the pressure may be increased again to further irradiate the top section of the package to obtain a uniform dose throughout the package. Thus, it should be understood that a pressure regulation cycle may include several increases and/or decreases during the relative movement between the object and the irradiation device.

The irradiation takes place at least during a portion of said pressure regulation cycle. This means that the irradiation may take a shorter period of time than the pressure regulation, or take the same time. Thus, the irradiation starts when the pressure regulation cycle starts or when the pressure regulation cycle has already started and ends at the same time as the pressure regulation cycle ends or earlier.

The method and device may also be used for irradiation of a web 60, for example irradiation for the purpose of sterilizing a packaging material web.

In general, the exemplary method comprises the steps of continuously conveying the web through a gaseous environment having a first pressure, the electron beam sterilizing device being provided in connection with said environment, and keeping a pre-determined second pressure at least in the environment nearest the sterilizing device during irradiation of the web. The device comprises an irradiation chamber enclosing a gaseous environment having a first pressure and means for continuously conveying the web through said gaseous environment. The electron beam sterilizing device is being provided in connection with said environment. Further, the device comprises means for keeping a pre-determined second pressure at least in the environment nearest the sterilizing device during irradiation of the web.

Figure 6:
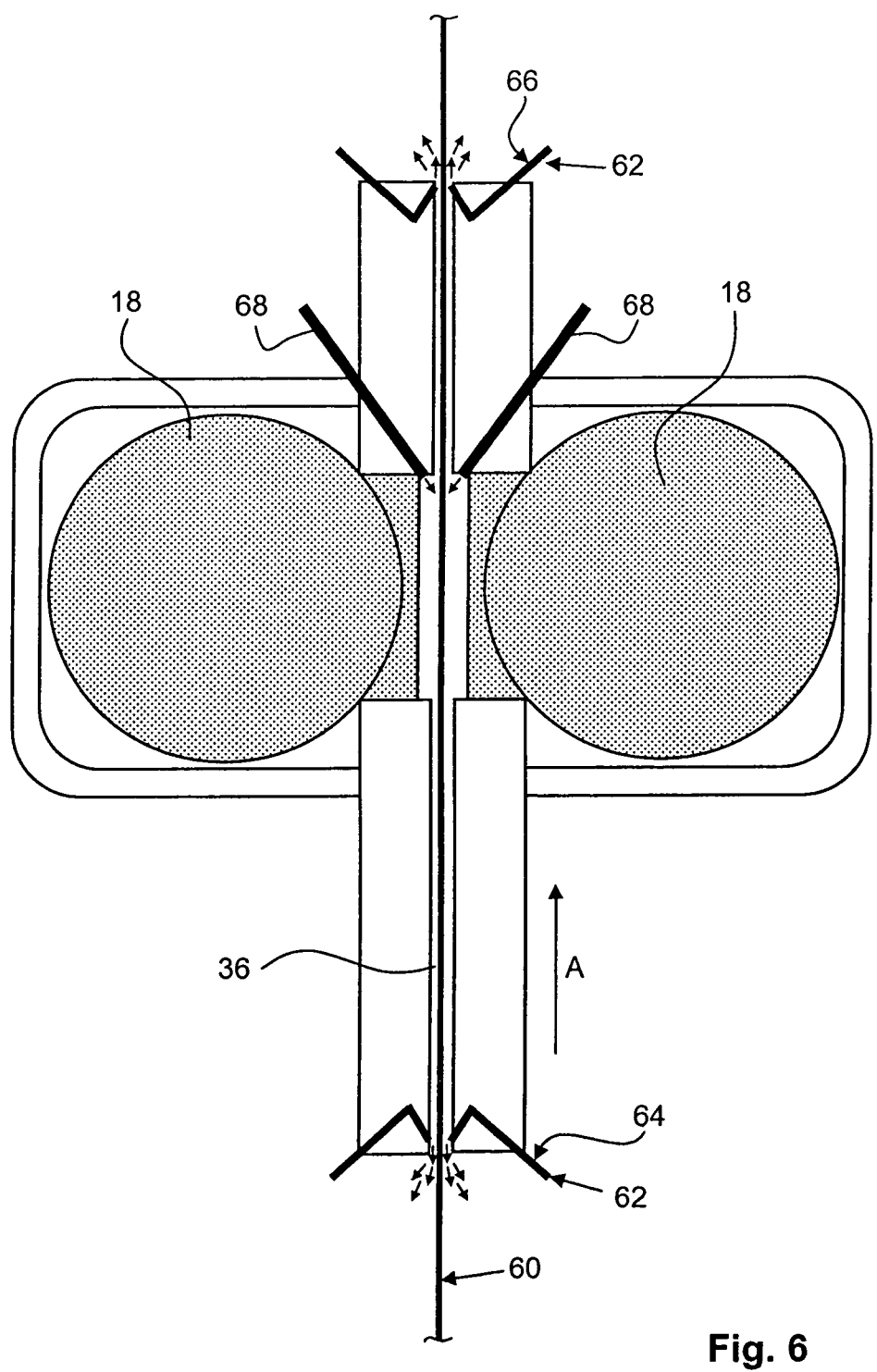

FIG. 6 shows such a fourth embodiment of the device.

The web 60 is continuously conveyed through the irradiation chamber 36 by any conventional conveying means (not shown). In this embodiment the chamber is a narrow tunnel 36. The web 60 is passed past at least one sterilizing device 18. In this case the web 60 is passed between two electron beam sterilizing devices 18, one on each side of the web, for double-sided irradiation. The web transportation direction is illustrated by the arrow A. For details on the overall design of an exemplary device reference is made to U.S. patent application publications 2006/0284111 and 2006/0145093.

The tunnel 36 is enclosing a gaseous environment having a first pressure.

Downstream and upstream the electron beam sterilizing devices 18 the device is provided with means 62 for keeping a pre-determined second pressure at least in the environment nearest the sterilizing device 18 during irradiation of the web 60. In this example these means 62 are means for reducing the pressure and are an upstream pair of air inlet nozzles 64 and a downstream pair of inlet nozzles 66.

The reduction of the pressure is accomplished through ejector effect. The nozzles 64, 66 inject air flows into the narrow tunnel 36. The air flows along the web together with the narrow tunnel 36 function as a pump and force the air in between the sterilizing devices 18 to be sucked out. Normally, this type of arrangement is called an ejector pump. Alternatively, other means may be used such as conventional pumps, for instance vacuum pumps, and these are then preferably located near or at the same locations as the nozzles 64, 66.

During irradiation a small amount of an inert gas such as nitrogen may preferably be supplied to the at least partly evacuated tunnel 36 between the sterilizing devices 18. The presence of nitrogen instead of air, comprising oxygen molecules, will effectively decrease the amount of ozone being created during the electron beam irradiation. The inert gas may be supplied through inlet ducts 68 connected to the tunnel 36 near the electron beam sterilizing devices 18.

After the web 60 has been irradiated, i.e. sterilized, in the irradiation chamber 36 it is to be formed into filled and sealed packages. Hence, the web 60 is further conveyed to a chamber (not shown) where it is formed into a tube by overlappingly sealing the longitudinal edges of the web. The tube is continuously filled with content via a product pipe extending into the tube from the end where the web has not yet been transformed into a tube. The filled tube is then transversally sealed and formed into cushions. The cushions are separated and formed into for example parallelepipedic containers.

This embodiment is a special case of the invention. The second pressure is preferably maintained as long as the sterilizing devices 18 are in operation irradiating the continuously passing web 60. If the irradiation is stopped, either temporarily or after a full production cycle, the second pressure is preferably not kept. Hence, in this embodiment, the previously described pressure regulation cycle extends over a longer period of time and the pressure is not substantially regulated during the time the irradiation is still going on.

It is also possible to use the present invention to sterilize a web provided with opening arrangements. Opening arrangements may be applied onto the web in the packaging machine before sterilization and before forming and filling operations. The opening arrangements may be of the type with a neck portion with a pouring aperture and a hinged lid covering said aperture. The opening arrangements may be formed by injection moulding them directly in holes punched in the web. The technique of pre-applying opening arrangements of this type is described in for example the international patent publication WO 98/18609. A web provided with pre-applied opening arrangements is a suitable object to irradiate (sterilize) with the method and device of the present invention. Preferably, a device according to the FIG. 6 embodiment may be used. The web may be conveyed through the irradiation chamber either continuously or intermittently. During continuous conveyance each opening arrangement may be adapted to pass by the electron beam sterilizing device, if necessary at a temporary slower velocity. During intermittent conveyance each opening arrangement may preferably be temporarily paused in front of the electron beam sterilizing device. In this way the irradiation dose may be enhanced over the opening arrangement in order to sufficiently sterilize all the irregular and inaccessible surfaces thereof. In addition, or alternatively, the effect of the irradiation over the opening arrangements may be enhanced by exposing the environment nearest the sterilizing device, and thereby also the portion of the web with the opening arrangement, to a pre-determined pressure regulation cycle. Such pressure regulation cycle may involve at least changing from a first pressure to a second pressure during irradiation and then back to the first pressure. The second pressure is lower than the first pressure.

Although the present invention has been described with respect to presently preferred embodiments, it is to be understood that various modifications and changes may be made without departing from the object and scope of the invention as defined in the appended claims.

One type of electron beam generator and one type of electron beam sterilizing device have been described, but it should be understood that they may both have another design or may function differently.

In the embodiments described the irradiation is made for sterilization purposes. However, it should be understood that the irradiation can be made for other purposes such as for example curing of ink or coatings.

In the FIG. 3 embodiment only one package 10 is shown. However, it is of course possible to irradiate a number of packages at the same time.

In the exemplary embodiment described in FIG. 4 the sterilizing chamber 36 is provided with only one treatment station, i.e. one sterilizing device 18. However, it should be understood that the irradiation chamber 36 may be provided with several sterilizing devices 18 for treating several packages at the same time. Further, the sterilizing devices 18 may be of different kinds for subsequently treating different portions of the package.

Further, in the exemplary embodiment described in FIG. 6 a web 10 is being irradiated. In an alternative, the web may comprise projecting opening devices that have been attached to the web or injection moulded directly on the web.

According to the invention the method comprises exposing the gaseous environment to a pre-determined pressure regulation cycle and exposing the object to irradiation at least during a portion of said pressure regulation cycle. Several alternatives have been presented how this pressure regulation could be accomplished. However, it should be understood that there are further alternatives how to make the pressure regulation as well, and that these alternatives are comprised in the scope of the claims.

The invention claimed is:

1. Method for irradiating a web of packaging material with electron beam irradiation from at least one electron beam sterilizing device, the method comprising:
continuously conveying the web in a conveying direction through a gaseous environment, the at least one electron beam sterilizing device being provided in said gaseous environment,
irradiating the web that is being continuously conveyed through an irradiation chamber by operating the at least one electron beam sterilizing device,
injecting air into the irradiation chamber at two spaced apart locations, one of which is upstream of the at least one electron beam sterilizing device relative to the conveying direction and the other of which is downstream of the at least one electron beam sterilizing device relative to the conveying direction, the injecting of the air comprising injecting air into the irradiation chamber at one location in one direction away from the at least one electron beam sterilizing device and injecting air into the irradiation chamber at an other location in an opposite direction away from the at least one electron beam sterilizing device to create an ejector effect which maintains a pre-determined pressure at least in a portion of the gaseous environment nearest the at least one electron beam sterilizing device during irradiation of the web, and
wherein the pre-determined pressure is below atmospheric pressure.

2. Method for irradiating a web of packaging material with electron beam irradiation from at least one electron beam sterilizing device, the method comprising:
conveying the web through a gaseous environment, the at least one electron beam sterilizing device being provided in connection with said gaseous environment,
exposing at least the gaseous environment nearest the at least one electron beam sterilizing device to a pre-determined pressure regulation cycle, and during irradiation exposing at least a portion of the web to said pressure regulation cycle so that the at least a portion of the web is exposed to a pressure change in the gaseous environment nearest the at least one electron beam sterilizing device while the web is being irradiated, and
wherein the pressure regulation cycle involves at least changing from a first total air pressure to a second total air pressure.

3. Method according to claim 2, wherein the second total air pressure is lower than the first total air pressure.

4. Method according to claim 2, wherein said portion of the web is provided with an opening arrangement.

5. Method according to claim 1, further comprising delimiting the gaseous environment around the portion of the web to be irradiated with the irradiation chamber.

6. Method according to claim 1, further comprising passing the web through the irradiation chamber, and directing the irradiation from the at least one electron beam sterilizing device into the irradiation chamber, the irradiation chamber being a narrow tunnel.

7. Method according to claim 1, further comprising forming the web after irradiation, into a tube by overlappingly sealing the longitudinal edges of the web, filling the tube with content, and transversally sealing the tube to form cushion-shaped packages containing the content.

8. Device for irradiating a web of packaging material with electron beam irradiation from at least one electron beam sterilizing device, the device comprising:
an irradiation chamber enclosing a gaseous environment,
means for continuously conveying the web in a conveying direction through said gaseous environment,
the electron beam sterilizing device being provided in said gaseous environment, and
an upstream inlet communicating with the gaseous environment upstream of the at least one electron beam sterilizing device relative to the conveying direction and a downstream inlet communicating with the gaseous environment downstream of the at least one electron beam sterilizing device relative to the conveying direction,
the upstream inlet being configured to inject the air into the irradiation chamber in one direction away from the at least one electron beam sterilizing device and the downstream inlet being configured to inject air into the irradiation chamber in an opposite direction away from the at least one electron beam sterilizing device to create an ejector effect which maintains a pre-determined total air pressure, below atmospheric pressure, at least in a portion of the gaseous environment nearest the electron beam sterilizing device during irradiation of the web.

9. Device for irradiating a web of packaging material with electron beam irradiation from at least one electron beam sterilizing device, the device comprising:
- an irradiation chamber enclosing a gaseous environment of a first total air pressure,
- means for conveying the web through said gaseous environment,
- the at least one electron beam sterilizing device being provided in connection with said gaseous environment, and
- means for exposing the gaseous environment nearest the at least one electron beam sterilizing device to a pre-determined pressure regulation cycle at least during irradiation of a portion of the web to change pressure in the gaseous environment from a first total air pressure to a second total air pressure so that the at least a portion of the web is exposed to a pressure change in the gaseous environment nearest the at least one electron beam sterilizing device while the web is being irradiated, the means for exposing comprising first and second air injection nozzles configured to inject air into the irradiation chamber in different directions.

10. Device according to claim 9, wherein the second total air pressure is lower than the first total air pressure.

11. Method according to claim 3, wherein the second total air pressure is below atmospheric pressure.

12. Device according to claim 10, wherein the second total air pressure is below atmospheric pressure.

13. Method for irradiating a web of packaging material comprising:
- conveying a web in a tunnel so that the web moves in a conveying direction through the tunnel, with an electron beam sterilizing device positioned along the tunnel;
- irradiating a portion of the web moving through an intermediate portion of the tunnel by operation of the electron beam sterilizing device,
- injecting air into the tunnel at two spaced apart locations while the moving web is being irradiated by the electron beam sterilizing device so that the injection of the air at the two spaced apart locations creates an ejector effect which maintains a pressure below atmospheric pressure at least in a portion of the tunnel nearest the electron beam sterilizing device, the two spaced apart locations at which the air is injected into the tunnel comprising a first location upstream of the electron beam sterilizing device relative to the conveying direction and a second location downstream of the electron beam sterilizing device relative to the conveying direction, the air being injected into the tunnel at the first location in a direction away from the intermediate portion of the tunnel and the air being injected into the tunnel at the second location in a different direction away from the intermediate portion of the tunnel.

14. Method according to claim 13, wherein the air is injected into the tunnel at the first location in a direction away from the electron beam sterilizing device and is injected into the tunnel at the second location in a direction away from the electron beam sterilizing device.

* * * * *